(12) United States Patent
Hofmann

(10) Patent No.: US 10,870,617 B2
(45) Date of Patent: Dec. 22, 2020

(54) METHOD FOR PREPARING DIALKYL DICARBONATES USING AMINE OXIDES

(71) Applicant: LANXESS Deutschland GmbH, Cologne (DE)

(72) Inventor: Christoph Hofmann, Cologne (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 16/451,532

(22) Filed: Jun. 25, 2019

(65) Prior Publication Data
US 2020/0010401 A1    Jan. 9, 2020

(30) Foreign Application Priority Data
Jul. 5, 2018    (EP) .................... 18181805

(51) Int. Cl.
| | | |
|---|---|---|
| *C07C 68/02* | (2006.01) | |
| *C07C 69/96* | (2006.01) | |
| *B01J 35/12* | (2006.01) | |
| *B01J 31/02* | (2006.01) | |

(52) U.S. Cl.
CPC ............ *C07C 68/02* (2013.01); *B01J 31/0271* (2013.01); *B01J 35/12* (2013.01); *C07C 69/96* (2013.01); *B01J 2231/49* (2013.01); *B01J 2531/002* (2013.01)

(58) Field of Classification Search
CPC .......... C07C 68/02; C07C 69/96; B01J 35/12; B01J 31/02
See application file for complete search history.

(56) References Cited

U.S. PATENT DOCUMENTS

| | | | |
|---|---|---|---|
| 3,326,958 A | 6/1967 | Curtius et al. | |
| 7,420,076 B2 * | 9/2008 | Prinz ...................... | C07C 68/02 558/264 |

OTHER PUBLICATIONS

European Search Report from corresponding European Application No. 18181805, dated Dec. 11, 2018, 2 pages.

* cited by examiner

*Primary Examiner* — Sun Jae Yoo
(74) *Attorney, Agent, or Firm* — Nicanor A. Kohncke

(57) ABSTRACT

The present invention relates to a method for preparing dialkyl dicarbonates from the corresponding alkyl chloroformates using specific amine oxides as catalysts.

15 Claims, No Drawings

METHOD FOR PREPARING DIALKYL DICARBONATES USING AMINE OXIDES

The present invention relates to a method for preparing dialkyl dicarbonates from the corresponding alkyl chloroformates using specific amine oxides as catalysts.

Dialkyl dicarbonates are used, for example, as catalysts for oxidizing sterically demanding amines, as constituents of electrolyte fluids or as constituents of antimicrobial reagents. Dialkyl dicarbonates are also referred to in the literature as dialkyl pyrocarbonates.

It is known from DE-B 1 210 853 to react carbonyl halides with organic hydroxyl compounds or alkali metal or alkaline earth metal salts thereof and organic solvents immiscible with water and at least equivalent amounts of alkali metal hydroxides or alkaline earth metal hydroxides or carbonates in a biphasic system, and using catalytic amounts of tertiary amines or quaternization products thereof, in which the amines or quaternization products thereof used are those which bear at least one nitrogen bonded ω-hydroxyalkyl, ω-hydroxyalkyl ether or ω-hydroxyalkyl polyether group.

DE-A 1 418 849 describes tertiary amines as particularly suitable catalysts for preparing acid derivatives, the tertiary nitrogen atoms of which are not sterically hindered, except tertiary amines which bear the same ω-hydroxyalkyl, ω-hydroxyalkyl ether or ω-hydroxyalkyl polyether group as substituents on the nitrogen. In addition to triethylamine and tri-n-butylamine, amines are therefore used here which bear at least one methyl group on the nitrogen, such as N-methyl-di-n-stearylamine for example. However, these catalysts have the disadvantage, inter alia, that they catalyze not only the formation but also the decomposition of the product, which results in a reduction in the yield. Some of these catalysts are also toxic, are poorly degraded in wastewater and can be difficult to remove from the reaction mixture due to their own decomposition during the reaction.

Known from EP-A 1747185 is a method for preparing dialkyl dicarbonates from alkyl haloformates by reaction with alkali metal hydroxides or alkaline earth metal hydroxides or carbonates, in which long-chain tertiary $C_6$-$C_{25}$-alkylamines are used. With these catalysts also, the yield of product was not completely satisfactory.

Therefore, there is a further need for a preparation process which affords the target product in high yield.

Surprisingly, it has been found that dialkyl dicarbonates can be obtained particularly advantageously from alkyl haloformates by reaction with alkali metal hydroxides or alkaline earth metal hydroxides or carbonates, if specific amine oxides of the formula (I) are used as catalyst. These are characterized by high catalytic activity, without causing decomposition of the end product. In addition, the yield of dialkyl dicarbonates using the compounds of the formula (I) is higher than with conventional tertiary amines.

Accordingly, the present invention relates to a method for preparing dialkyl dicarbonates by reacting the corresponding alkyl haloformates with alkali metal hydroxides or alkaline earth metal hydroxides and/or carbonates in the presence of organic solvents immiscible with water and in the presence of a catalyst, characterized in that the catalyst used is at least one compound of the formula (I)

(I)

in which
$R^1$ and $R^2$=straight-chain or branched $C_1$-$C_6$-alkyl,
$R^3$=straight-chain or branched $C_{10}$-$C_{22}$-alkyl,
wherein $R^1$ and $R^2$ are each mutually independent and may be the same or different.

In carrying out the method according to the invention, preference is given to using as catalyst a compound of the formula (I), in which $R^1$ and $R^2$=methyl, ethyl, n-propyl, s-propyl, n-butyl, s-butyl, isobutyl or t-butyl and $R^3$=straight-chain or branched $C_{10}$-$C_{18}$-alkyl.

Particular preference is given to using as catalysts compounds of the formula (I) where $R^1$ and $R^2$=methyl and $R^3$=$C_{12}$-$C_{18}$-alkyl.

In one embodiment of the method according to the invention, the catalyst used is a compound of the formula (I), in which $R^3$ is in each case straight-chain or branched dodecanyl, undecanyl, tridecanyl, tetradecanyl, pentadecanyl, hexadecanyl, heptadecanyl, octadecanyl, nonadecanyl, eicosanyl, icosanyl, heneicosanyl or dodoconyl. Preferably, $R^3$=dodecanyl, tetradecanyl, hexadecanyl and octadecanyl.

In a further embodiment of the method according to the invention, the catalyst is a compound of the formula (I) in which $R^1$ and $R^2$=methyl and $R^3$=dodecanyl, tetradecanyl, and hexadecanyl.

In carrying out the method according to the invention, it is also possible to use any desired mixtures of the catalysts.

In a further preferred embodiment, the catalysts used are mixtures of compounds of the formula (I) which comprise different radicals $R^3$ having straight-chain or branched $C_{10}$-, $C_{11}$-, $C_{12}$-, $C_{13}$-, $C_{14}$-, $C_{15}$-, $C_{16}$-, $C_{17}$- or $C_{18}$-alkyl.

Even more preference is given to using mixtures of compounds of the formula (I) which include different radicals $R^3$ having straight-chain or branched $C_{12}$-, $C_{14}$- and $C_{16}$-alkyl and in which $R^1$ and $R^2$=methyl.

In a further preferred embodiment, the catalysts used are mixtures of compounds of the formula (I), which comprise different radicals $R^3$ having straight-chain or branched $C_{12}$-, $C_{14}$- and $C_{16}$-alkyl and $R^1$ and $R^2$=methyl and in which the content of the compound where $R^3$=$C_{12}$-alkyl is from 60% by weight and 80% by weight and the content of the compound where $R^3$=$C_{14}$-alkyl is from 19% by weight and 30% by weight and the content of the compound where $R^3$=$C_{16}$-alkyl is from 1% by weight and 10% by weight, based on the total weight of the compound of the formula (I) used.

In a further preferred embodiment, the compounds of the formula (I) used are mixtures of lauryldimethyldiamine oxide (N,N-dimethyldodecan-1-amine oxide), myristamine oxide (N,N-dimethyltetradecan-1-amine oxide) and hexadecanyldimethylamine oxide (N,N-dimethylhexadecan-1-amine oxide). These catalysts are preferably used at a content of 60% by weight to 80% by weight lauryldimethylamine oxide, 19% by weight to 30% by weight myristamine oxide and 1% by weight to 10% by weight hexadecanyldimethylamine oxide, based on the total weight of the compounds of the formula (I) used.

In a further preferred embodiment, the catalysts used can be mixtures of the compounds of the formula (I), in which the radicals $R^1$, $R^2$ and $R^3$, in the context of the above disclosure, may be combined in any desired manner. In a further preferred embodiment, the catalysts are dissolved in water, optionally in the presence of a solvent miscible with water, prior to use in the method according to the invention. The solvents miscible with water used are preferably alcohols, such as in particular glycols. The compounds of the formula (I) are preferably present at a concentration between 25% by weight to 75% by weight in water or in the mixtures with water and the solvent miscible with water.

The tertiary amines typically used to prepare the catalysts are readily oxidized to amine oxides by hydrogen peroxide or a peroxycarboxylic acid. Catalysts such as N,N-dimethyldodecan-1-amine oxide are commercially available and are marketed, for example, under the names Barlox 12 or Barlox 1260 by Lonza. Their preparation processes are also known to those skilled in the art.

The method according to the invention provides the preparation of dialkyl dicarbonates of the formula (II)

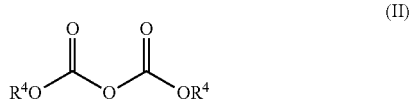
(II)

in which
$R^4$ is straight-chain or branched $C_1$-$C_{20}$-alkyl,
by reacting alkyl haloformates of the formula (III)

(III)

in which
Hal is halogen, preferably F, Cl, Br, I, especially chlorine, and
$R^4$ is straight-chain or branched $C_1$-$C_{20}$-alkyl.

In the formulae (II) and (III), $R^4$ is preferably straight-chain or branched $C_1$-$C_8$-alkyl, particularly preferably a radical —CH—$R^5R^6$, wherein $R^5$ and $R^6$ are each independently H or straight-chain or branched $C_1$-$C_7$-alkyl. $R^4$ is particularly methyl, ethyl, n-propyl, isopropyl, n-butyl or isobutyl. $R^4$ is particularly preferably methyl, such that dimethyl dicarbonate is obtained as compound of the formula (II).

Alkali metal hydroxides or alkaline earth metal hydroxides or carbonates include, for example, LiOH, NaOH, KOH, $LiCO_3$, $Na_2CO_3$, $K_2CO_3$. Preference is given to using alkali metal hydroxides such as sodium and potassium hydroxide which are preferably used in the form of aqueous solutions. For example, 1 to 50% by weight aqueous alkali metal hydroxide solutions can be used. Preference is given to 5 to 35% by weight solutions, particular preference to 10 to 25% by weight solutions. The alkali metal hydroxides or alkaline earth metal hydroxides or carbonates are preferably used in amounts of 80 to 120 mol %, based on the haloformate used. This amount is particularly preferably in the range of 90 to 115 mol %, especially preferably in the range of 95 to 115 mol %.

Organic solvents immiscible with water include, for example, aliphatic and aromatic hydrocarbons, halogenated hydrocarbons, ethers or esters immiscible with water and also dialkyl carbonates. Preference is given to cyclohexane, toluene, xylene, methylene chloride and diethyl ether, especially toluene and methylene chloride. Very particular preference is given to using toluene.

The organic solvent immiscible with water can be used, for example, in amounts from 20 to 90% by weight, preferably from 30 to 80% by weight, particularly preferably from 40 to 80% by weight, based on the haloformate of the formula (III).

The catalyst of the formula (I) is generally used in an amount from 0.1 to 7 mol %, preferably from 0.5 to 5 mol %, based on haloformate of the formula (III). The catalyst of the formula (I) is even more preferably used in an amount from 0.5 to 3 mol %.

The method according to the invention can be carried out in a pressure range of 1 to 10 bar, preferably 1 to 1.5 bar.

The reaction temperature can be, for example, between −10° C. and the boiling temperature (at standard pressure) of the haloformate used. It is preferably in the range 0 to 50° C. Even more preferably, the reaction temperature is between 15° C. and 19° C.

While carrying out the method according to the invention, it is advantageous to ensure thorough mixing, for example by using stirrers, baffles or circulation pumps.

The method according to the invention can be carried out both batchwise and continuously. In the batchwise mode, the reaction is carried out preferably in a stirred tank. In this context, depending on the size of the batch and the cooling power present, the reaction is generally terminated after 10 minutes to 3 hours.

The method according to the invention is preferably carried out continuously using a stirred tank, stirred tank cascade or a tubular reactor. The mean residence time in the reactor in this case is generally between 1 and 60 minutes, preferably between 6 and 45 minutes and particularly preferably between 10 and 30 minutes.

After carrying out the method according to the invention, optionally after cooling, the reaction mixture separates into two phases. The organic phase comprises, in addition to the solvent, the dialkyl dicarbonate produced and possibly low amounts of unreacted haloformate as well as the catalyst. In addition to water, the aqueous phase comprises the inorganic salts formed.

The product is already present at high purity, such that, besides the phase separation, no further distillative separation is required.

By using the catalysts used in accordance with the invention, dialkyl dicarbonates can be prepared in high yield.

EXAMPLES

Example 1

A mixture of 18.87 g (0.2 mol) of methyl chloroformate (MC) and 14.83 g of toluene is initially charged in a reaction vessel and 3.57 g of Barlox 12 (Lonza, Basel) (0.0045 mol) ((30% by weight solution of 70% lauryldimethyldiamine oxide (amine oxide of the formula (I) where $R^1$ and $R^2$=methyl, $R^3$=$C_{12}$-alkyl), 26% myristamine oxide (amine oxide of the formula (I) where $R^1$ and $R^2$=methyl, $R^3$=$C_{14}$-alkyl and 4% hexadecanyldimethylamine oxide (amine oxide of the formula (I) where $R^1$ and $R^2$=methyl, $R^3$=$C_{16}$-alkyl) in water) and 62.73 g of ca. 14% NaOH (0.22 mol) are then introduced.

This mixture is reacted with vigorous stirring at 17° C. After ca. 20 min, the phases were separated.

The crude yield of dimethyl dicarbonate is ca. 95% based on the amount of MC used.

Comparative Example 1 Using a Tertiary Amine as Catalyst

The present example is already known in similar form from EP 1747185 A (Example 3).

A mixture of 20.41 g (0.22 mol) of MC and 14.78 g of toluene is initially charged in a reaction vessel and then 0.54 g (0.0015 mol) of Alamine 308 (triisooctylamine) and 64.27 g of ca. 14% NaOH (0.22 mol) are introduced.

This mixture is reacted with vigorous stirring at 12° C. After ca. 20 min, the phases were separated.

The crude yield of dimethyl dicarbonate is ca. 91% based on the amount of MC used.

What is claimed is:

1. A method for preparing dialkyl dicarbonates, comprising reacting an alkyl haloformate with at least one alkali metal hydroxide, alkaline earth metal hydroxide and/or carbonate in the presence of at least one organic solvent immiscible with water and in the presence of a catalyst, wherein the catalyst is at least one compound of the formula (I)

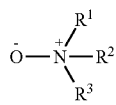
(I)

in which
$R^1$ and $R^2$ is straight-chain or branched $C_1$-$C_6$-alkyl,
$R^3$ is straight-chain or branched $C_{10}$-$C_{22}$-alkyl,
wherein $R^1$ and $R^2$ may be the same or different.

2. The method according to claim 1, wherein $R^3$ is selected from the group of straight-chain or branched dodecanyl, undecanyl, tridecanyl, tetradecanyl, pentadecanyl, hexadecanyl, heptadecanyl, octadecanyl, nonadecanyl, eicosanyl, icosanyl, heneicosanyl and dodoconyl.

3. The method according to claim 1, wherein $R^3$ is selected from the group of straight-chain or branched $C_{10}$-, $C_{11}$-, $C_{12}$-, $C_{13}$-, $C_{14}$-, $C_{15}$-, $C_{16}$-, $C_{17}$-, and $C_{18}$-alkyl.

4. The method according to claim 1, wherein $R^1$ and $R^2$ are selected from the group of methyl, ethyl, n-propyl, s-propyl, n-butyl, s-butyl, isobutyl and t-butyl and $R^3$ is straight-chain or branched $C_{10}$-$C_{18}$-alkyl.

5. The method according to claim 1, wherein $R^1$ and $R^2$ are methyl and $R^3$ is $C_{10}$-$C_{16}$-alkyl.

6. The method according to claim 1, wherein $R^1$ and $R^2$ are methyl and $R^3$ is selected from the group of dodecanyl, tetradecanyl, and hexadecanyl.

7. The method according to claim 1, wherein $R^3$ is selected from the group of straight-chain or branched $C_{12}$-, $C_{14}$- and $C_{16}$-alkyl and $R^1$ and $R^2$ are methyl and wherein the content of the compound where $R^3$=$C_{12}$-alkyl is from 60% by weight to 80% by weight and the content of the compound where $R^3$=$C_{14}$-alkyl is from 19% by weight to 30% by weight and the content of the compound where $R^3$=$C_{16}$-alkyl is from 1% by weight to 10% by weight, based on the total weight of the compound of the formula (I).

8. The method according to claim 1, wherein the dialkyl dicarbonates are of formula (II)

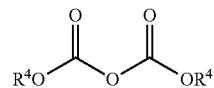
(II)

in which
$R^4$ is straight-chain or branched $C_1$-$C_{20}$-alkyl,
and are formed by reacting alkyl haloformates of formula (III)

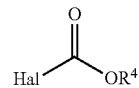
(III)

in which
Hal is halogen and
$R^4$ is straight-chain or branched $C_1$-$C_{20}$-alkyl.

9. The method according to claim 8, wherein $R^4$ is methyl, ethyl, n-propyl, isopropyl, or n-butyl or isobutyl.

10. The method according to claim 1, wherein the alkali metal hydroxides or alkaline earth metal hydroxides and/or carbonates are in the form of aqueous solutions.

11. The method according to claim 1, wherein the at least one organic solvent immiscible with water is selected from the group of aliphatic and aromatic hydrocarbons, chlorinated hydrocarbons, dialkyl carbonates, ethers and esters immiscible with water.

12. The method according to claim 1, wherein the catalyst is present in the amount of 0.1 to 7 mol %, based on the haloformate.

13. The method according to claim 1, wherein the reaction is carried out at a temperature of 15° C. and 19° C. (at standard pressure).

14. The method according to claim 1, wherein the reaction is carried out in a continuous mode of operation.

15. The method according to claim 1, further comprising, after completion of the reaction whereby a reaction mixture is formed, phase separating the dialkyl dicarbonate whereby an organic phase is formed and subsequently performing a multi-stage distillation of the organic phase.

* * * * *